United States Patent
Potvin

(10) Patent No.: US 9,880,076 B2
(45) Date of Patent: Jan. 30, 2018

(54) COMPOUND SAMPLING SYSTEM AND METHOD FOR SAMPLING A COMPOUND USING SAME

(71) Applicant: MORIN ÉNERTECH INC., La Baie (CA)

(72) Inventor: Frédéric Potvin, Jonquière (CA)

(73) Assignee: MORIN ENERTECH INC., La Baie, Quebec (CA)

( * ) Notice: Subject to any disclaimer, the term of this patent is extended or adjusted under 35 U.S.C. 154(b) by 0 days.

(21) Appl. No.: 14/786,458

(22) PCT Filed: Apr. 22, 2014

(86) PCT No.: PCT/CA2014/050391
§ 371 (c)(1),
(2) Date: Oct. 22, 2015

(87) PCT Pub. No.: WO2014/172790
PCT Pub. Date: Oct. 30, 2014

(65) Prior Publication Data
US 2016/0069780 A1   Mar. 10, 2016

Related U.S. Application Data

(60) Provisional application No. 61/814,624, filed on Apr. 22, 2013.

(51) Int. Cl.
*G01N 1/22*   (2006.01)
*G01N 1/24*   (2006.01)
(Continued)

(52) U.S. Cl.
CPC ......... *G01N 1/2247* (2013.01); *G01N 1/2273* (2013.01); *G01N 1/24* (2013.01);
(Continued)

(58) Field of Classification Search
CPC ...... G01N 1/2247; G01N 1/2273; G01N 1/24; G01N 1/26; G01N 2001/225; G01N 33/0016; G01P 5/02
See application file for complete search history.

(56) References Cited

U.S. PATENT DOCUMENTS 3,213,669 A * 10/1965 Taft .................... G01N 30/82
141/130
4,226,115 A * 10/1980 Williams ............ G01N 1/2273
340/12.5
(Continued)

FOREIGN PATENT DOCUMENTS

| EP | 2015270 | * | 1/2009 | |
| GB | 1385307 A | * | 2/1975 | ............... C21B 7/24 |
| GB | 2205551 A | * | 12/1988 | ........... G01N 1/2035 |

OTHER PUBLICATIONS

Amer, Hassanein H., and Ramz M. Daoud. "Fault-secure multidetector fire protection system for trains." IEEE Transactions on Instrumentation and Measurement 56.3 (2007): 770-777.*
(Continued)

*Primary Examiner* — Lisa Caputo
*Assistant Examiner* — Punam Roy
(74) *Attorney, Agent, or Firm* — Merchant & Gould P.C.

(57) ABSTRACT

A compound sampling system has a guiding assembly extending along a sampling path and a shuttle unit having a displacement mechanism engageable to the guiding assembly and configured to displace the shuttle unit onto the guiding assembly. The shuttle unit also includes at least one sampling component configured to monitor a gaseous substance and collect sampling data relative to the compound in the gaseous substance. The sampling system further includes a control system in communication with the shuttle unit. The control system includes a controller communicably coupled to the displacement mechanism and controlling the displace-
(Continued)

ment of the shuttle unit along the sampling path. A method of sampling a compound uses the sampling system.

21 Claims, 7 Drawing Sheets

(51) Int. Cl.
*G01N 1/26* (2006.01)
*G01N 33/00* (2006.01)
*G01P 5/02* (2006.01)

(52) U.S. Cl.
CPC ........... *G01N 1/26* (2013.01); *G01N 33/0016* (2013.01); *G01P 5/02* (2013.01); *G01N 2001/225* (2013.01)

(56) References Cited

U.S. PATENT DOCUMENTS

| | | | |
|---|---|---|---|
| 4,577,518 A | 3/1986 | Fong et al. | |
| 5,206,818 A | 4/1993 | Speranza | |
| 5,363,707 A * | 11/1994 | Augenblick | G01N 30/06 73/863.81 |
| 5,416,321 A * | 5/1995 | Sebastian | B25J 5/005 250/288 |
| 5,420,440 A * | 5/1995 | Ketler | G01N 21/534 250/573 |
| 5,832,411 A | 11/1998 | Schatzmann et al. | |
| 6,558,540 B2 * | 5/2003 | Berger | B01D 11/0203 210/198.2 |
| 2002/0070169 A1 * | 6/2002 | Berger | B01D 11/0203 210/656 |
| 2007/0050850 A1 * | 3/2007 | Katoh | G06F 21/31 726/27 |
| 2009/0015820 A1 * | 1/2009 | Bohe | G01N 1/2226 356/51 |
| 2012/0018152 A1 * | 1/2012 | Zuilekom | E21B 34/08 166/264 |
| 2012/0053838 A1 * | 3/2012 | Andrews | E21B 49/082 702/8 |
| 2015/0273691 A1 * | 10/2015 | Pollack | G01N 35/00623 348/143 |

OTHER PUBLICATIONS

SatheeshKumar, P. "An efficient way of monitoring and controlling the train parameters using Multi-core Embedded Processors (MCEP)." Computer Science and Information Technology (ICCSIT), 2010 3rd IEEE International Conference on. vol. 9. IEEE, 2010.*

International Search Report for International Patent Application No. PCT/CA2014/050391 dated Jul. 15, 2014.

* cited by examiner

COMPOUND SAMPLING SYSTEM AND METHOD FOR SAMPLING A COMPOUND USING SAME

CROSS REFERENCE TO RELATED APPLICATION

This application is a National Stage Application of PCT/CA2014/050391, filed Apr. 22, 2014, which claims the benefit under 35 U.S.C. § 119(e) of U.S. provisional patent application No. 61/814,624 which was filed on Apr. 22, 2013 and which applications are incorporated herein by reference. To the extent appropriate, a claim of priority is made to each of the above disclosed applications.

FIELD OF THE INVENTION

The present invention relates to the field of sampling systems. More particularly, it relates to an automated compound sampling system and to a method of sampling a compound using the same.

BACKGROUND

In many jurisdictions, it is compulsory for industries to measure the fugitive emissions of specific compounds produced from industrial activities and which may, for example and without being limitative, contribute to air pollution and/or climate change.

For example, in many countries, it is compulsory for industries emitting hydrogen fluoride (HF) to measure the fugitive emission thereof, in order to determine the net emissions of HF released in the environment. Indeed, in the production of aluminum, HF emissions are generally generated by reduction cells in the electrolysis process. The majority of these emissions are captured and treated in dry scrubbing centers. However, fugitive emissions generally still remain and can subsequently escape to the environment through the roof vents of the potrooms or smelter buildings.

Current known methods for measuring the fugitive emissions of a compound commonly include cassette samplers positioned proximate to the outlet vents of the corresponding building and which require periodical manual retrieval by a worker. Sampling methods using this type of sampler are therefore usually worker extensive and require workers to access elevated sections of the building where the environment is hot and may contain high acid gas concentration, which is undesirable. Expensive access structures are also usually required for the workers to access these elevated sections where the cassette samplers are located. Such methods also tend to have relatively high error ratio.

In view of the above, there is a need for an improved sampling system and a method of sampling a compound using the same which would be able to overcome or at least minimize some of the above-discussed prior art concerns.

SUMMARY OF THE INVENTION

According to a first general aspect, there is provided a compound sampling system which comprises a guiding assembly extending along a sampling path, a shuttle unit and a control system. The shuttle unit has a displacement mechanism engageable to the guiding assembly and configured to displace the shuttle unit onto the guiding assembly and at least one sampling component configured to monitor a gaseous substance and collect sampling data relative to the compound in the gaseous substance. The control system is in communication with the shuttle unit and includes a controller communicably coupled to the displacement mechanism and controlling the displacement of the shuttle unit along the sampling path.

In an embodiment, the shuttle unit and the control system each comprise at least one transceiver configured to transmit the sampling data from the at least one sampling component to the control system.

In an embodiment, the controller is configured to transmit control signals to the at least one sampling component, via the transceivers, to adjust at least one sampling parameter of the at least one sampling component.

In an embodiment, the at least one sampling component comprises at least one of a vacuum pump, a flow controller and a sampling cassette.

In an embodiment, the at least one sampling component further comprises an anemometer.

In an embodiment, the controller of the control system is configured to receive airflow velocity data from the anemometer and send control signals to the flow controller to adjust an inward airflow to substantially match the inward airflow with an airflow velocity indicated by the airflow data.

In an embodiment, the shuttle unit comprises a protection chamber with at least one of the at least one sampling component at least partially housed therein and a thermal control unit configured to maintain a temperature inside the protection chamber within a predetermined operating temperature range.

In an embodiment, the thermal control unit includes a temperature sensor and at least one of a cooling unit and a heating unit.

In an embodiment, the shuttle unit includes a collection chamber configured to receive and temporarily maintain the gaseous substance, the collection chamber being configured to promote at least one of particles agglomeration of the gaseous substance and condensation of the gaseous substance.

In an embodiment, the collection chamber includes a plurality of baffles spaced apart from one another and configured to increase the collision rate of fine particles of the gaseous substance.

In an embodiment, each one of the plurality of baffles include apertures at an end thereof, the baffles being oriented such that the apertures of adjacent baffles are at opposite ends thereof.

In an embodiment, the sampling system comprises at least two shuttle units engageable to the guiding assembly and displaceable therealong.

In an embodiment, the sampling path extends along a wall of a building to a shuttle accessible position.

In an embodiment, the shuttle accessible position comprises a lower position proximate to a lower end of the guiding assembly.

According to another general aspect, there is also provided a method of sampling a compound. The method includes the steps of: mounting at least one shuttle unit having at least one sampling component to a guiding assembly extending along a sampling path; displacing the at least one shuttle unit along the sampling path; and controlling the displacement of the at least one shuttle unit along the sampling path using a controller of a control system.

In an embodiment, the method further comprises the steps of: monitoring a gaseous substance using at least one of the at least one sampling component; collecting sampling data of the compound found in the gaseous substance from the at least one of the at least one sampling component; and transmitting the sampling data to the control system.

In an embodiment, the at least one shuttle unit comprises a displacement mechanism with an actuator and the step of controlling the displacement of the at least one shuttle unit along the sampling path comprising the steps of: receiving the sampling data from the at least one of the at least one sampling component at the control system; evaluating at least one of the velocity of the gaseous substance, the flow profile of the gaseous substance and the concentration profile of the gaseous substance, based on the received sampling data by the control system; and transmitting control signals to the actuator of the displacement mechanism of the at least one shuttle unit based on the at least one of the evaluated velocity of the gaseous substance, flow profile of the gaseous substance and concentration profile of the gaseous substance.

In an embodiment, the at least one sampling component collects the sampling data in accordance with at least one sampling parameter and the method further comprises the step of controlling the at least one sampling parameter of at least one of the at least one sampling component.

In an embodiment, the method further comprises the step of adjusting the at least one sampling parameter of at least one of the at least one sampling component based on the received sampling data.

In an embodiment, the at least one sampling component comprises an anemometer and a flow controller and the step of adjusting the at least one sampling parameter of at least one of the at least one sampling component based on the received sampling data comprising the steps of measuring an airflow velocity using the anemometer and controlling the flow controller to adjust an inward airflow to substantially match the measured airflow velocity.

In an embodiment, the at least one shuttle unit comprises a protection chamber and a thermal control unit and the method further comprises the steps of: sensing a temperature in the protection chamber of the at least one shuttle unit; comparing the sensed temperature with at least one temperature constraint; and activating the thermal control unit to adjust the temperature if the sensed temperature is outside of the at least one temperature constraint.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which.

DETAILED DESCRIPTION

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of the sampling system and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the sampling system, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

Figure 1:
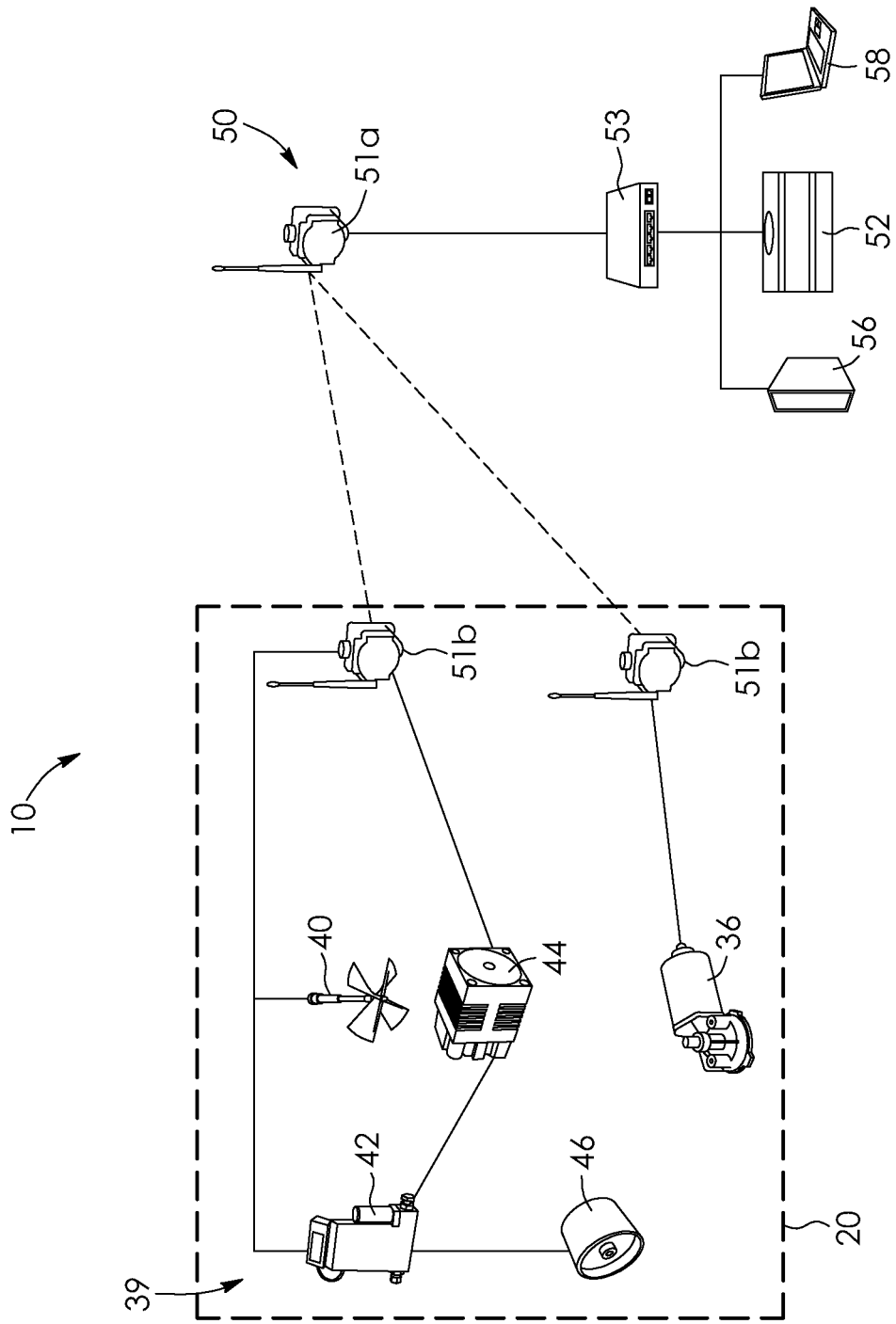
FIG. 1 is a schematic representation of the components of a sampling system according to an embodiment.

Referring generally to FIG. 1, in accordance with an embodiment, there is provided a sampling system 10 comprising at least one shuttle unit 20 movable along a path, as will be described in more details below. The control system 50 controls the operation of the shuttle unit 20 and its components, as will once again be described in more details below. The shuttle unit 20 collects sampling data regarding a compound to be sampled. The sampling data are collected by sampling components 39 mounted to or housed in a body of the shuttle unit 20 and which monitor a gaseous substance in the environment of the shuttle unit. In the course of the present document, it will be understood that the compound to be sampled is a compound, such as, a chemical compound or fine particles, found in the gaseous substance, i.e. a substance that is predominantly a gas, but which may include liquid droplets or fine particles, such as a suspension or a colloid.

In an embodiment, in order to sample the desired compound in the environment of the shuttle unit 20 and collect sampling data relative to the sampled compound, the sampling components 39 of a shuttle unit 20 include an anemometer 40 for measuring the airflow velocity; and a vacuum pump 44, a flow controller 42 and a sampling cassette 46 for controlling the inward airflow and measuring a quantity of the compound to be sampled. In the course of the present description, the term inward airflow is understood to describe the velocity of the gas flowing through the sampling cassette 46. In an embodiment and without being limitative, the anemometer 40 is a 8371-UM anemometer from KATREM, the vacuum pump 44 is a DVH145-Y1 pump from MEDO, and the flow controller 42 is a GFC17A-VADL4-E controller from AALBORG. One skilled in the art will understand that, in an alternative embodiment, other sampling components different from the one mentioned above can be provided.

In an embodiment, the collected sampling data are communicated to the control system 50. The control system 50 is configured to receive, process, and report the sampling data. The sampling data can be reported in a process state and/or an unprocessed state. In an embodiment, the control system 50 is configured and programmed to control the displacement of the shuttle unit 20. The displacement of the shuttle unit can be controlled based on the sampling data received from the sampling components 39. The combination of the shuttle unit 20 and the control system 50 operates to form the sampling system 10. As mentioned above, the sampling system 10 can include more than one (or a plurality) of shuttle units 20. In the embodiment shown, the control system 50 is a remote system communicating to the shuttle unit using radio signals, as will be described in more details below. However, one skilled in the art will understand that, in an embodiment (not shown) the control system may be an embedded system or a combination of an embedded system and a remote system.

In the embodiment shown, each one of the shuttle unit 20 and the control system 50 of the sampling system 10 comprises at least one wireless transceiver 51a, 51b using radio frequency signals to communicate with one another through a wireless communications network such as, without being limitative, a Wi-Fi® network. One skilled in the art will understand that, in an alternative embodiment, other wireless communications means or method, such as, without being limitative radio communications systems, or wired communications means or method can be used for communications between the shuttle unit 20 and the control system 50.

In an embodiment, the control system 50 includes a controller 52 operative to control each one of the shuttle unit(s) 20 and the associated sampling components 39. The controller 52 receives data from the transceiver 51a of the control system 50. The received data are obtained from the shuttle unit 20 and the associated sampling components 39. The data are sent to the transceiver 51a by the transceiver 51b mounted to the shuttle unit 20. Similarly, the controller 52 also sends operating instructions generated by the controller to at least one of an actuator of a displacement mechanism of the shuttle unit 20, which will be described in more details below, and the sampling components 39 of the shuttle unit 20 via the transceivers 51b, 51b. In the embodiment shown, the control system 50 is connected to the transceiver 51a over a network. In such an embodiment a network switch 53 can be provided between the controller 52 and the transceiver 51a.

In an embodiment, the control system 50 further includes a user interface 58 which allows users to access the sampling data on a communications device such as, without being limitative a computer, a smartphone, a tablet or the like. One skilled in the art will understand that, the sampling data may be processed by a processor of the control system 50 prior to the display via the user interface 58, in order to compute the data and display relevant information related to the sampled substance, such as, for example and without being limitative, net emissions, fugitive emissions or any other information that can be inferred from the sampling data and may be relevant to the users. In an embodiment, unprocessed data may also be displayed via the user interface 58. In an embodiment, the user interface 58 may also be used by a user to input control commands regarding the shuttle unit 20 and the associated sampling components 39 and communicate the control commands to the shuttle unit 20, via the controller 52.

The control system 50 further includes a storage unit 56 for storing the sampling data collected by the sampling components 39 and transmitted to the control system 50 via the transceivers 51a, 51b. The storage unit 56 can also store event-related data, i.e. data related to the operation of the shuttle unit such as, for example and without being limitative any event causing a stoppage thereof. Such event-related data may be subsequently processed, analyzed, and/or used, for example and without being limitative, for troubleshooting purposes and process improvement.

One skilled in the art will understand that the control system 50 may include additional components which allow communication between the control system 50 and the shuttle unit(s) 20, such as to receive and display relevant information to the user effectively, or transmit data to the shuttle unit(s) 20, or report the collected data. Additional functionalities such as, without being limitative alert generation, remote access, system configuration, and user access management may be provided by the control system 20. One skilled in the art will understand that, in an embodiment, the control system 50 is one of a computer or a computer system, which can be a standalone system or a distributed system. In an embodiment, the control system is configured to receive sampling data from another source than the above-described shuttle unit 20. Such sampling data may subsequently be used to control the shuttle unit 20 or at least one of the sampling components thereof.

As will be easily understood, the sampling data gathered by each one of a plurality of shuttle units 20 can be collected, processed, and aggregated by the control system 50, in order to provide relevant sampling data to the users via the user interface 58.

The above described sampling system 10 allows each shuttle unit 20 to operate as an autonomous sampling unit controlled by the control system 50. In an embodiment, each shuttle unit 20 may be displaced along a path to reach a representative sampling position which corresponds to an optimal position (or most representative position) to perform the sampling of the compound. The location of the representative sampling position may be determined according to a variety of external parameters such as, outer temperature variations, i.e. temperature variations in the environment where sampling occurs and sampling data previously collected using the corresponding shuttle unit 20. In an embodiment, the position of each shuttle unit 20 may be automatically adapted such that each shuttle unit 20 is maintained at the representative sampling position during a time period, and can subsequently be displaced toward another representative sampling position.

The representative sampling positions are usually located in elevated sections of a building and, more particularly, are often proximate to the outlet vents. As will be described in more details below, the system allows an automatic displacement of the shuttle unit 20 between the representative sampling position and a shuttle unit accessible position, such as, without being limitative, a lowered position. When the shuttle unit 20 is positioned in the shuttle unit accessible position, easy access to the sampling components 39 is provided. For instance, if the shuttle unit accessible position is the lowered position, access to the sampling components 39 is provided from the ground, without requiring that the users access the elevated sections of the building where sampling is carried out.

In another embodiment, the positioning and displacement of each shuttle unit 20 may be controlled by the controller 52 of the control system 50 according to at least one of the following parameters: the velocity of the gaseous substance, the flow profile of the gaseous substance, the concentration profile of the compound, or any other additional relevant parameter(s). In an embodiment, these parameters are determined based on the sampling data collected using at least one of the anemometer 40, the sampling cassette 46, the flow controller 42, and the thermocouple (not shown) measuring the temperature outside of the shuttle unit 20.

In such an embodiment, the sampling data from at least one of the sampling components are communicated to the control system, either by transmission of sampling data by one of the sampling components or by input of data from a third party user or system. The control system evaluates at least one of the velocity of the gaseous substance, the flow profile of the gaseous substance and the concentration profile of the compound based on the received sampling data and transmits control signals to an actuator of a displacement mechanism of the at the one shuttle unit, which will be described in more details below, in response to the evaluation of these parameters. In an embodiment, the positioning and displacement of each shuttle unit 20 may be controlled by the controller 52 of the control system 50 according to different parameters evaluated based on the sampling data collected by the sampling components 39.

In an embodiment, during operation, at least one sampling parameter of at least one of the sampling components 39 is automatically adjusted by the transmission of a control signal from the controller 52 of the control system 50 to a controller of a corresponding one of the sampling components 39.

In an embodiment, this automatic adjustment of the sampling parameters of the sampling components 39 allows isokinetic sampling by the shuttle unit 20 of the sampling system 10. In such an embodiment, the flow controller 42 is programmed and/or controlled in order to adjust the inward airflow based on the airflow velocity of the air stream in the vicinity of the shuttle unit 20, measured by the anemometer 40, such that the inward airflow substantially matches the ascending airflow velocity, taking into account the displacement of the shuttle unit 20, and thereby allow the isokinetic sampling. In such an embodiment, the controller 52 of the control system 50 is configured to receive airflow velocity data from the anemometer 40 and send a control signal to the flow controller 42 to adjust the inward airflow to substantially match the inward airflow with the airflow velocity indicated by the airflow velocity data.

Figure 2:
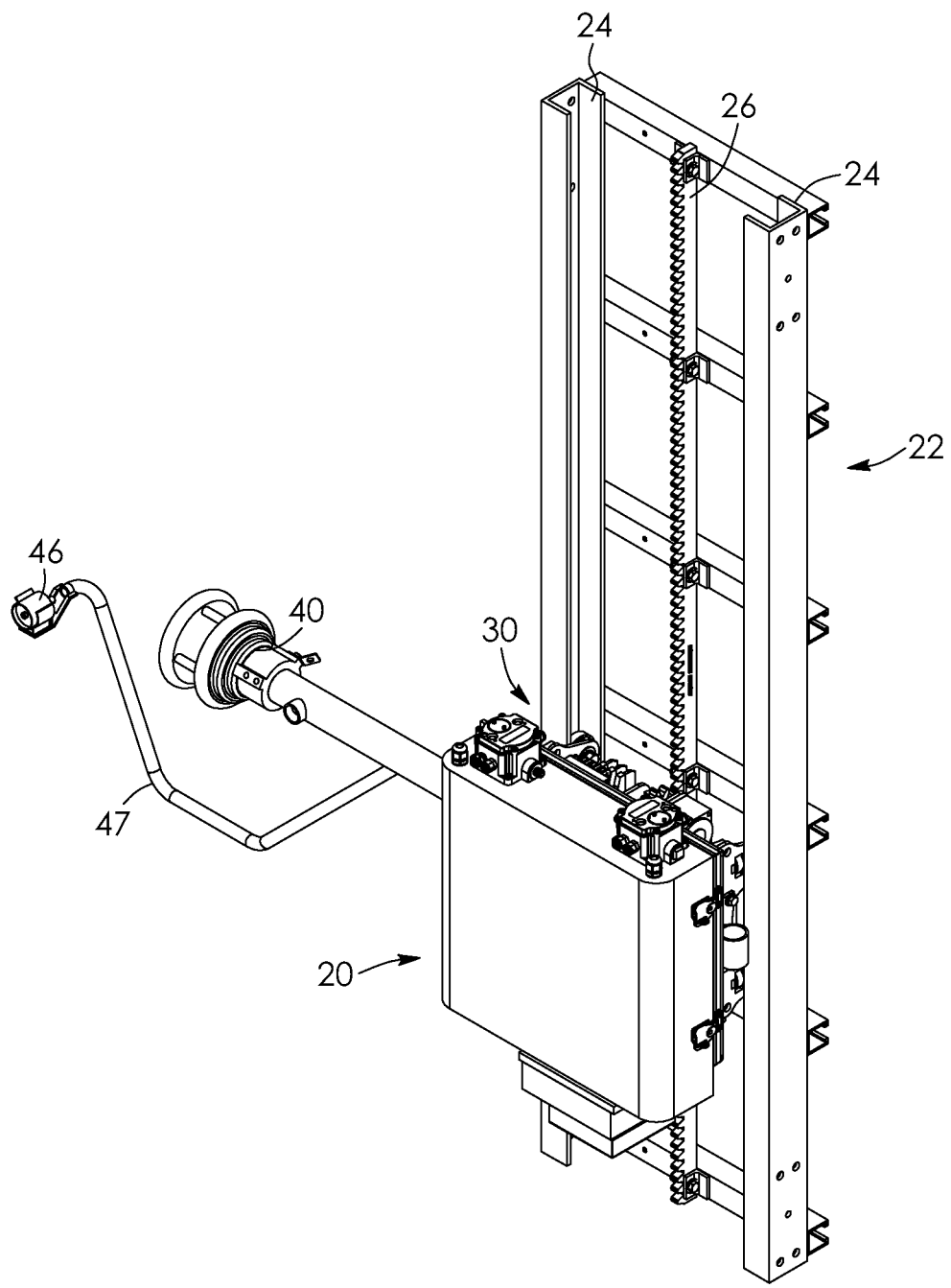
FIG. 2 is a perspective view of a shuttle unit of the sampling system of FIG. 1 mounted on a guiding assembly.
Figure 3:
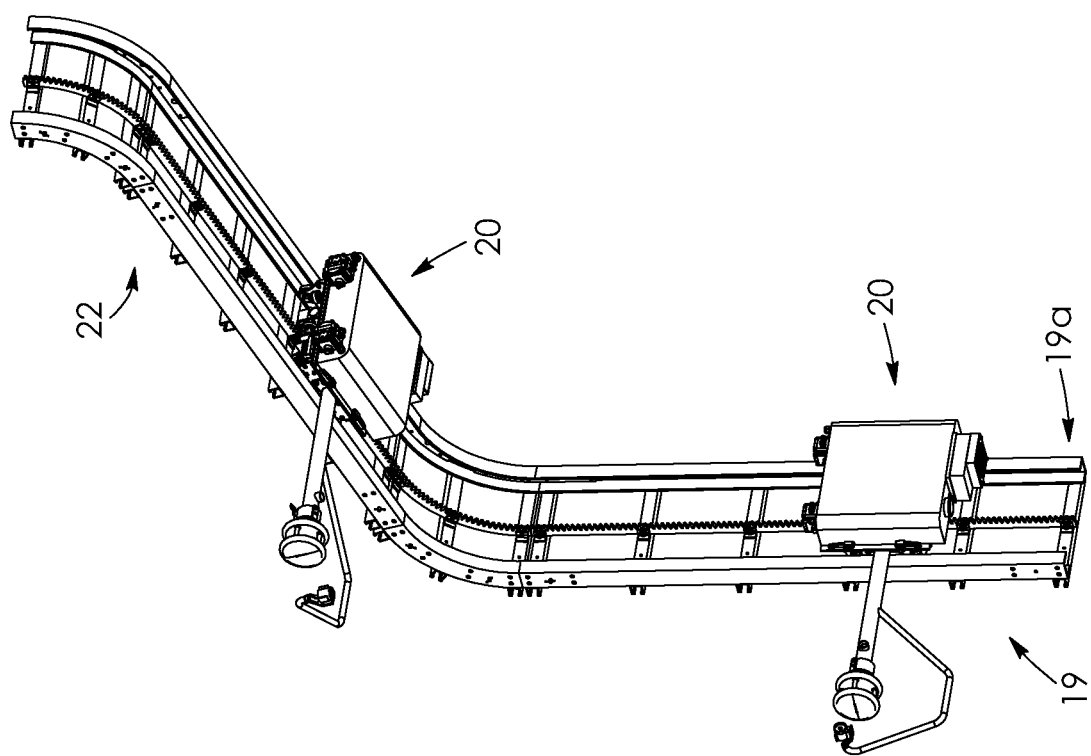
FIG. 3 is a perspective view of two shuttle units of the sampling system of FIG. 1 mounted on the guiding assembly.

Now referring to FIGS. 2 and 3, there is shown a shuttle unit 20, of a sampling system 10, mounted on a guiding assembly 22 in accordance with an embodiment. The guiding assembly 22 defines a path on which the shuttle unit 20 can travel. As mentioned above, the sampling system 10 can include more than one shuttle unit 20. Thus, a plurality of shuttle units 20 can be mounted on the guiding assembly 22, as shown in FIG. 3. In an embodiment, the guiding assembly 22 onto which the shuttle unit 20 is displaceable is a rail. However, one skilled in the art would understand that other types of guiding assembly, such as without being limitative a H-beam, can be provided. In an embodiment, the guiding assembly 22 defines a sampling path which extends along the walls and the ceiling of a building where sampling of the compound found in a gaseous substance is performed. For instance, in an embodiment, the sampling path extends from the shuttle accessible position 19, such as the lowered position where the shuttle unit 20 is proximate to a lower end 19a of the guiding assembly 22 and is easily accessible by a user, and up to an upper end (not shown) at or close to the ceiling of the building, or any other suitable sampling position. In order to allow easy installation of the guiding assembly 22 in a building, the guiding assembly 22 may comprise a plurality of sections connected to one another by known connecting means such as, without being limitative, male-female members with locking pins, nuts and bolts or the like. One skilled in the art will understand that the sections may also be connected permanently to one another, for example and without limitative by welding, soldering or the like.

Figure 4:
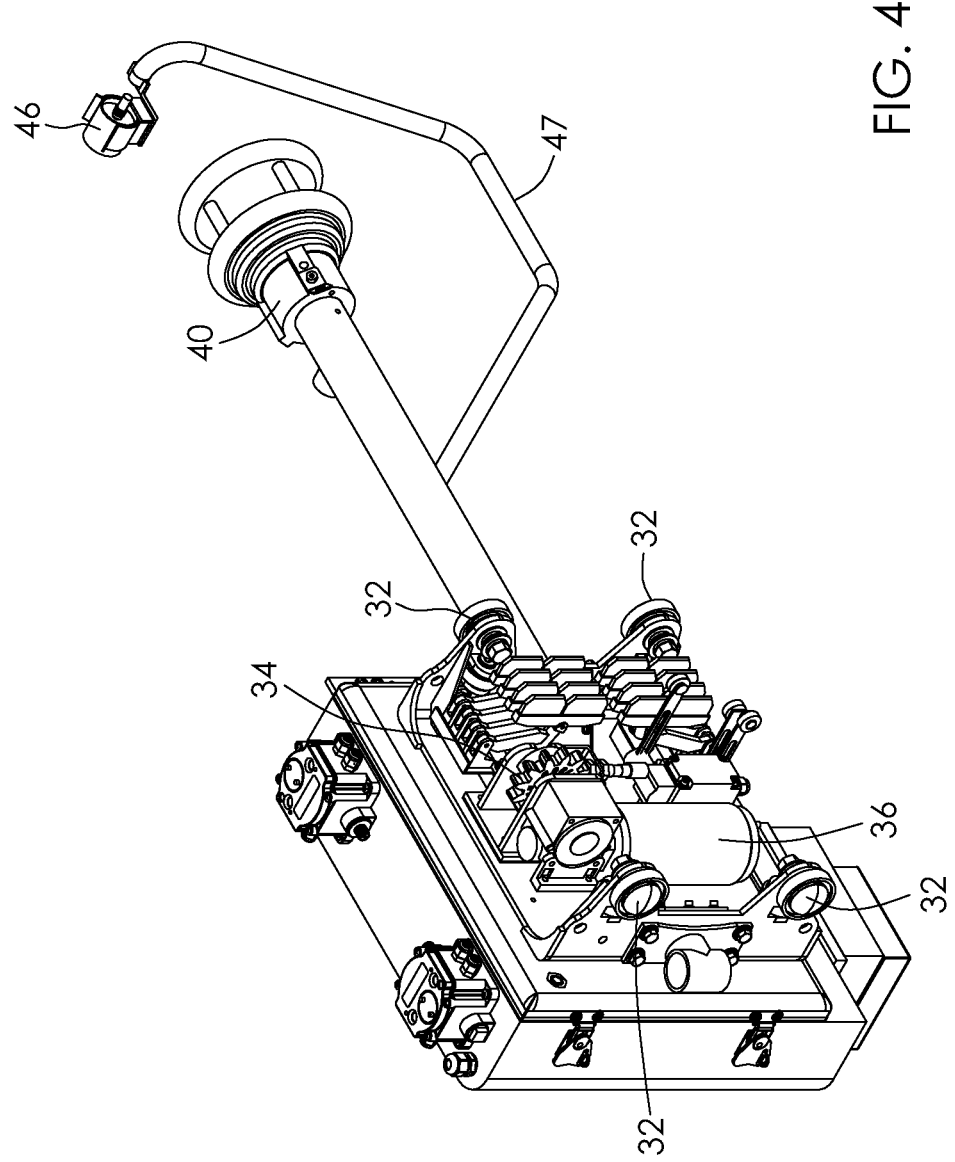
FIG. 4 is a rear perspective view of the shuttle unit of FIG. 2, wherein the shuttle unit is configured in a closed configuration.

Referring to FIGS. 2 to 4, each shuttle unit 20 includes a displacement mechanism 30 cooperating with the guiding assembly 22 for displacing the shuttle unit 20 thereabout. In an embodiment, the displacement mechanism 30 includes two sets of free rolling wheels 32. Each set of wheels 32 is rotatably configured to be inserted into a peripheral channel 24 formed in the guiding assembly 22 in order to allow the shuttle unit 20 to be maintained against the guiding assembly 22 and be captive of the guiding assembly 22, while being displaceable therealong. Such a configuration avoids the risks of detachment of the shuttle unit 20 from the guiding assembly 22 during operation. In the embodiment shown, the displacement mechanism 30 further includes a toothed wheel 34 operatively connected to an actuator 36, such as an electric motor, which controls the rotation of the toothed wheel 34. The toothed wheel 34 is engageable with a corresponding toothed guide 26, mounted between the peripheral channels 24 of the guiding assembly 22, in order to drive the shuttle unit 20 along the guiding assembly 22. A rotation of the toothed wheel 34 in a first direction drives the shuttle unit 20 in a first direction and the rotation of the toothed wheel in the second direction drives the shuttle unit 20 in a second opposite direction. One skilled in the art will understand that, in alternative embodiments, a different displacement mechanism 30 than the one described above and resulting in the controlled displacement of the shuttle unit 20 along the guiding assembly 22 can be provided.

In an embodiment, control of the positioning of the shuttle unit 20 by the controller 52 of the control system 50 is performed by the transmission of control signals from the controller 52 of the control system 50 to a controller of the actuator 36 of the displacement mechanism 30.

Figure 5:
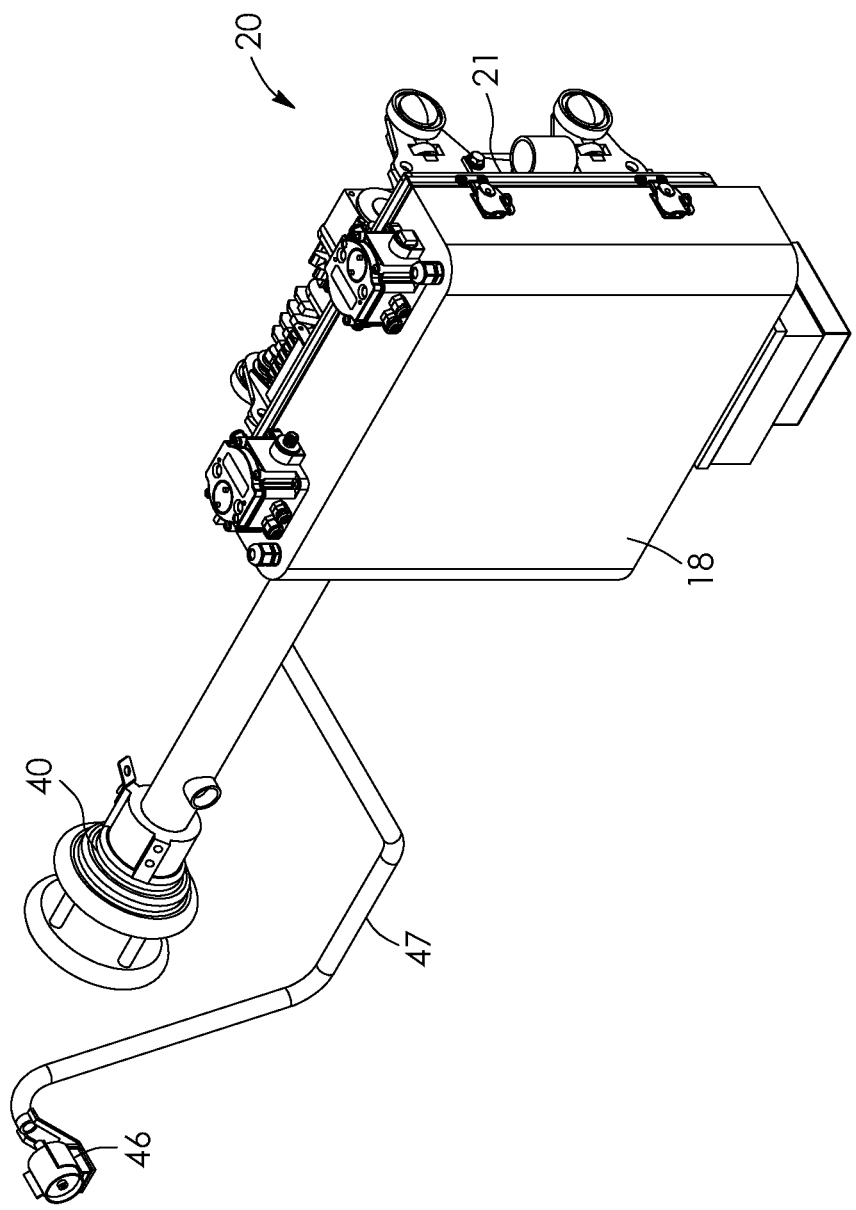
FIG. 5 is a front perspective view of the shuttle unit of FIG. 4.

The shuttle unit 20 includes a main body 21 and a hard outer cover 18, removably mounted to the main body 21. In an embodiment, the hard outer cover 18 is hingedly mounted to the main body 21 and defines therewith a protection chamber 27. The hard outer cover 18 is configurable in a closed configuration (shown in FIGS. 4 and 5) and an open configuration (shown in FIG. 6). In the closed configuration, it provides protection to the sampling components 39 contained in the protection chamber 27. In the open configuration, it provides access to the sampling components 39 contained in the protection chamber 27. In the embodiment shown, the anemometer 40 and the sampling cassette 46 are mounted to the main body 21 and extend outwardly therefrom, i.e. they are not contained in the protection chamber 27 in the closed configuration of the hard outer cover 18. A sampling canal 47 connects the sampling cassette 46 to the main body 21 and allows the intake of the gaseous substance into the protection chamber 27. The other sampling components 39 are contained in the protection chamber 27.

Figure 6:
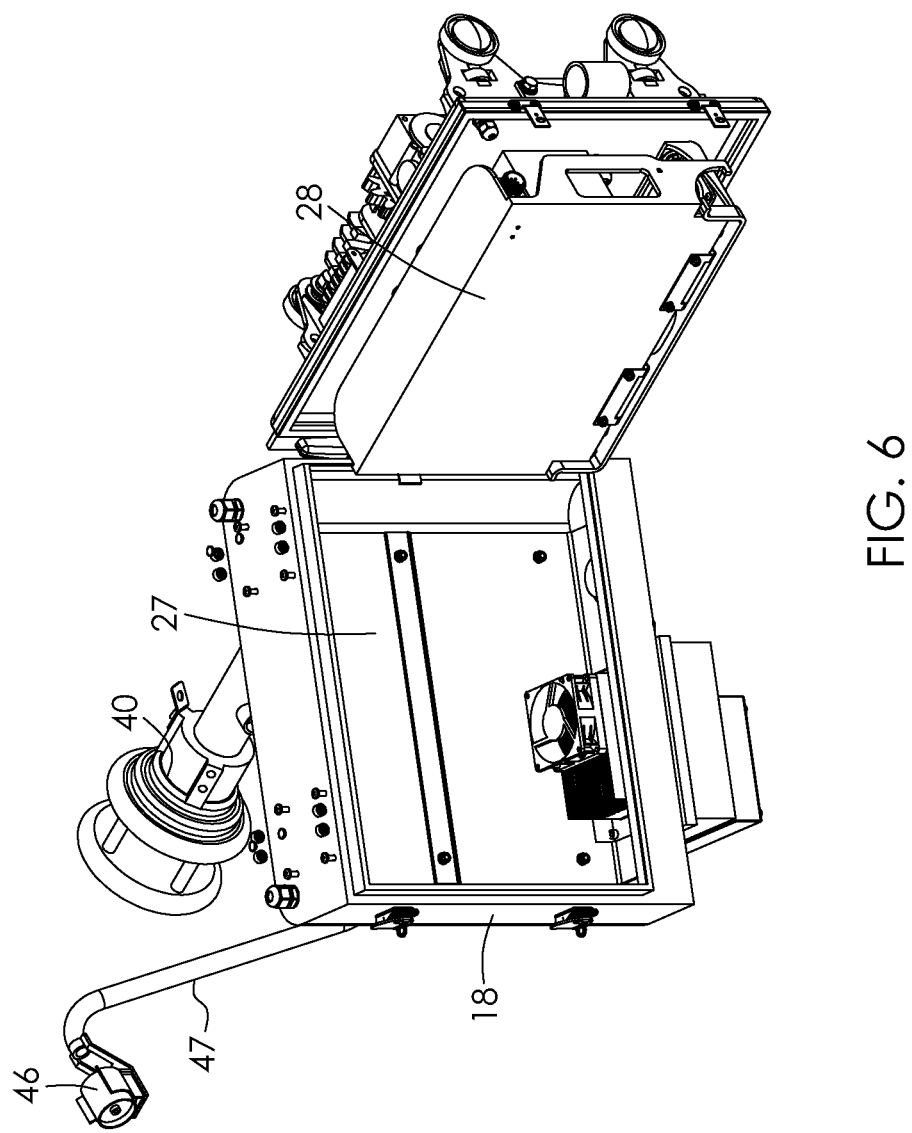
FIG. 6 is a front perspective view of the shuttle unit of FIG. 4, wherein the shuttle unit is configured in an open configuration.

In the embodiment of FIG. 6, the sampling components 39, contained in the protection chamber 27, are mounted to a removable rack 28, insertable in the protection chamber 27 and securable to the main body 21. In FIG. 6, the sampling components 39 are located between the main body 21 and the removable rack 28, and therefore are not shown.

One skilled in the art would therefore understand that in the embodiment shown, the compound is sampled by an airflow being drawn into the sampling cassette 46, flowing through the sampling canal 47 towards the flow controller 42. The airflow subsequently flows through the flow controller 42 and into the pump 44, before being rejected in the environment, outside of shuttle unit 20.

In an embodiment, each shuttle unit 20 is also provided with a thermal control unit (not shown). The thermal control unit includes a temperature sensor and at least one of a cooling unit and a heating unit which operate to monitor the temperature of the shuttle unit 20 and to control the temperature in the protection chamber 27 of the shuttle unit 20. In an embodiment, the heating and cooling unit can be embodied by a fully reversible solid state heating/cooling unit which can perform either one of heating, cooling or both. The temperature in the protection chamber 27 of the shuttle unit 20 is typically maintained within the operating temperature range prescribed by the manufacturers of the sampling components 39 located in the protection chamber 27, or of other precision components provided therein, such as, without being limitative between about 0° Celsius and about 55° Celsius.

The temperature sensor measures the temperature in the protection chamber 27 of the shuttle unit 20 and compares the measured temperature with at least one temperature constraint which, in an embodiment, substantially corresponds to the above-mentioned operating temperature range. If the measured temperature is outside of the at least one temperature constraint, the corresponding one of the cooling unit or the heating unit is activated. In other words, if the temperature control unit senses that the temperature in the protection chamber 27 is above an upper threshold, the cooling unit is activated to lower the temperature of the protection chamber 27 of the shuttle unit 20. Similarly, when the temperature control unit senses that the temperature in the protection chamber 27 is below a lower threshold, the heating unit is activated to increase the temperature of the protection chamber 27.

In an embodiment, the compound to be sampled is hydrogen fluoride (HF). However, one skilled in the art will understand that the above described system may be used for sampling other chemical compounds or than HF such as, without being limitative, sulfur dioxide ($SO_2$), benzene ($C_6H_6$), carbon dioxide ($CO_2$), ethylene oxide ($C_2H_4O$), nitrous oxide ($N_2O$), trichloroethylene ($C_2HCl_3$), fluorocarbons and fine particles in ambient air.

Figure 7:
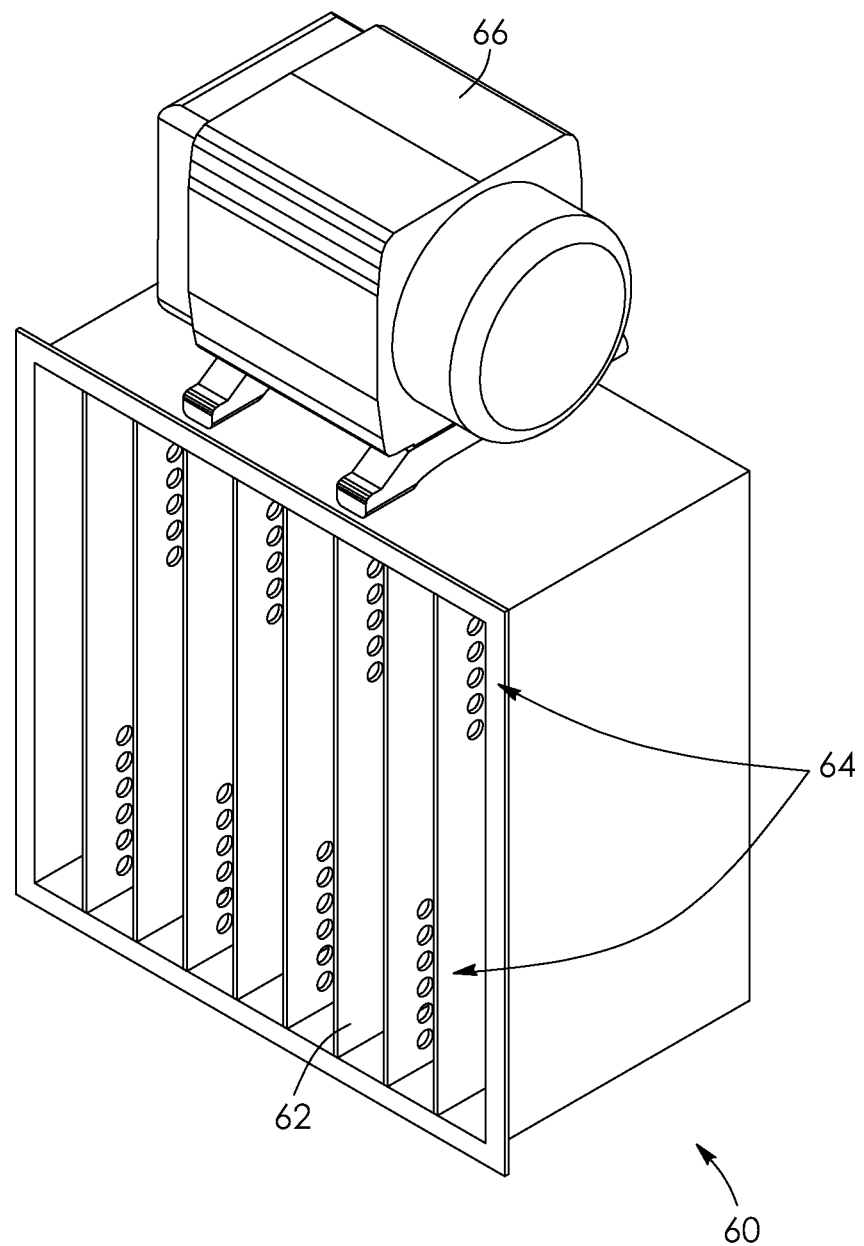
FIG. 7 is a perspective view of a collection chamber of the shuttle unit, according to an embodiment, and shown with a front face removed.

Referring to FIG. 7, in an embodiment the shuttle unit 20 can further include a collection chamber 60 for receiving a gaseous substance and promote either one of the agglomeration of the fine particles or the condensation of the gaseous substance prior to sampling of a compound therein. The collection chamber 60 includes an inlet port (not shown) allowing inflow of the gaseous substance and an outlet port (not shown) allowing gaseous substance outflow. The inlet port is connected to a pump 66 and can be selectively open/close in order to allow inflow of substance in the collection chamber 60. Similarly, the outlet port can be selectively open/close in order to allow outflow of substance in the collection chamber 60. In an embodiment, the collection chamber 60 includes a plurality of baffles 62 spaced apart from one another and configured to increase the collision rate of the fine particles as the received gaseous substance circulates inside the collection chamber 60. In an embodiment, the baffles 62 include apertures 64 at one end thereof, the baffles 62 being oriented such that the apertures 64 of adjacent baffles 62 are at opposite ends thereof. In an embodiment, the temperature inside the collection chamber 60 is adjusted by a temperature control unit operating similarly to the above described thermal control unit such as to promote particles agglomeration or condensation of the substance. In operation a first sampling is performed such that the gaseous substance is dragged into the collection chamber 60, the gaseous substance is retained inside the collection chamber 60 for a residency time period and is subsequently released therefrom for a subsequent sampling of the compound of the gaseous substance found inside the collection chamber 60. Such a collection chamber 60 is provided in embodiments where the compound to be sampled is composed of fine particles in the ambient air which require agglomeration before sampling of the fine particles can occur or when a condensable gas requires a certain degree of condensation prior to sampling of a compound therein.

One skilled in the art would therefore understand that, in the embodiment shown, the compound is sampled by an airflow being drawn into the collection chamber 60 and circulating inside the collection chamber 60 for a residency time period. In an embodiment, a percentage of the internal volume of the gaseous substance contained inside the collection chamber 60 may be replaced periodically during the residency time period. Subsequently to the residency time period, at least a portion of the gaseous substance of the collection chamber is drawn in turn into the sampling cassette 46, into the flow controller 42 and into the pump 44, before being rejected in the environment, outside of shuttle unit 20. Evidently connecting canals can be provided between the above mentioned components for circulation of the gaseous substance. In such an embodiment, the sampling cassette 46 can be located inside the protection chamber 27.

In an embodiment (not shown), the shuttle unit 20 may also include a gas tight container, such as a bag, for receiving the gaseous substance. In an embodiment, the gas tight container is removably connected to an output of the pump 44 and collects the gaseous substance being rejected by the pump 44 subsequently to the sampling of the compound. Therefore, the gaseous substance may be collected by the shuttle unit 20 (in the gas tight container) and the gas tight container can subsequently be removed for subsequent analysis of the gaseous substance collected therein.

In another embodiment (not shown), the shuttle unit 20 may also include sorbent tubes to trap and retain the compound(s) of interest and subsequently extract the collected compounds for analysis. In such an embodiment, the sorbent tubes can be connected between the sampling cassette 46 and the flow controller 42 in the flow path of the gaseous substance.

The above described assembly allows easy replacement of the sampling cassette 46 by a user and easy access to additional sampling components 39 for repair and/or calibration. As previously mentioned, the guiding assembly 22 has a shuttle accessible position 19, i.e. a position easily accessible by a user, which results in easy access to the shuttle unit 20 and the sampling components 39 by a user.

In an embodiment, each shuttle unit 20 includes an internal unit position controller which is activated following an occurrence of a failure at the shuttle unit 20, such as, without being limitative a communications issue, an electrical issue or the like. The internal position controller is configured to control the actuator 36 of the displacement mechanism 30 to move the shuttle unit 20 to the shuttle accessible position 19 following the occurrence of the above-mentioned failure. In other words, upon occurrence of a failure, such as a communications failure between the shuttle unit 20 and the control system 50, the shuttle unit 20 is configured to automatically return to the shuttle accessible position 19 in order to avoid having to climb to reach an unresponsive shuttle unit 20.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A compound sampling system for sampling a compound in a building, the compound sampling system comprising:
    a guiding assembly extending along a sampling path including at least a portion extending in an elevated section of the building;
    a shuttle unit having a displacement mechanism engageable to the guiding assembly and configured to displace the shuttle unit onto the guiding assembly and at least one sampling component configured to monitor a gaseous substance and collect sampling data relative to the compound in the gaseous substance; and
    a control system in communication with the shuttle unit, the control system including a controller communicably coupled to the displacement mechanism and controlling the displacement of the shuttle unit along the sampling path.

2. The compound sampling system of claim 1, wherein the shuttle unit and the control system each comprise at least one transceiver configured to transmit the sampling data from the at least one sampling component to the control system.

3. The compound sampling system of claim 2, wherein the controller is configured to transmit control signals to the at least one sampling component, via the transceivers, to adjust at least one sampling parameter of the at least one sampling component.

4. The compound sampling system of claim 1, wherein the at least one sampling component comprises at least one of a vacuum pump, a flow controller and a sampling cassette.

5. The compound sampling system of claim 4, wherein the at least one sampling component further comprises an anemometer.

6. The compound sampling system of claim 5, wherein the controller of the control system is configured to receive airflow velocity data from the anemometer and send control signals to the flow controller to adjust an inward airflow to substantially match the inward airflow with an airflow velocity indicated by the airflow data.

7. The compound sampling system of claim 1, wherein the shuttle unit comprises a protection chamber with at least one of the at least one sampling component at least partially housed therein and a thermal control unit configured to maintain a temperature inside the protection chamber within a predetermined operating temperature range.

8. The compound sampling system of claim 7, wherein the thermal control unit includes a temperature sensor and at least one of a cooling unit and a heating unit.

9. The compound sampling system of claim 1, wherein the shuttle unit includes a collection chamber configured to receive and temporarily maintain the gaseous substance, the collection chamber being configured to promote at least one of particles agglomeration of the gaseous substance and condensation of the gaseous substance.

10. The compound sampling system of claim 9, wherein the collection chamber includes a plurality of baffles spaced apart from one another and configured to increase the collision rate of fine particles of the gaseous substance.

11. The compound sampling system of claim 10, wherein each one of the plurality of baffles include apertures at an end thereof, the baffles being oriented such that the apertures of adjacent baffles are at opposite ends thereof.

12. The compound sampling system of claim 1, wherein the sampling system comprises at least two shuttle units engageable to the guiding assembly and displaceable therealong.

13. The compound sampling system of claim 1, wherein the sampling path extends along a wall of the building to a shuttle accessible position.

14. The compound sampling system of claim 13, wherein the shuttle accessible position comprises a lower position proximate to a lower end of the guiding assembly.

15. A method of sampling a compound in a building, the method including the steps of:
    mounting at least one shuttle unit having at least one sampling component to a guiding assembly extending along a sampling path, with at least a portion of the sampling path extending in an elevated section of the building;
    displacing the at least one shuttle unit along the sampling path; and
    controlling the displacement of the at least one shuttle unit along the sampling path using a controller of a control system.

16. The method of claim 15, further comprising the steps of:
    monitoring a gaseous substance using at least one of the at least one sampling component;
    collecting sampling data of the compound found in the gaseous substance from the at least one of the at least one sampling component; and
    transmitting the sampling data to the control system.

17. The method of claim 16, wherein the at least one shuttle unit comprises a displacement mechanism with an actuator, and wherein the step of controlling the displacement of the at least one shuttle unit along the sampling path comprises the steps of:
    receiving the sampling data from the at least one of the at least one sampling component at the control system;
    evaluating at least one of the velocity of the gaseous substance, the flow profile of the gaseous substance and the concentration profile of the compound, based on the received sampling data by the control system; and
    transmitting control signals to the actuator of the displacement mechanism of the at least one shuttle unit based on the at least one of the evaluated velocity of the gaseous substance, flow profile of the gaseous substance and concentration profile of the compound.

18. The method of claim 15, wherein the at least one sampling component collects the sampling data in accordance with at least one sampling parameter, the method further comprising the step of controlling the at least one sampling parameter of at least one of the at least one sampling component.

19. The method of claim 18, further comprising the step of adjusting the at least one sampling parameter of at least one of the at least one sampling component based on the received sampling data.

20. The method of claim 19, wherein the at least one sampling component comprises an anemometer and a flow controller and wherein the step of adjusting the at least one sampling parameter of at least one of the at least one sampling component based on the received sampling data comprises the steps of measuring an airflow velocity using the anemometer and controlling the flow controller to adjust an inward airflow to substantially match the measured airflow velocity.

21. The method of claim 15, wherein the at least one shuttle unit comprises a protection chamber and a thermal control unit, the method further comprising the steps of:
- sensing a temperature in the protection chamber of the at least one shuttle unit;
- comparing the sensed temperature with at least one temperature constraint; and
- activating the thermal control unit to adjust the temperature if the sensed temperature is outside of the at least one temperature constraint.

* * * * *